United States Patent
á Wengen

[19]

[11] Patent Number: 5,935,167
[45] Date of Patent: Aug. 10, 1999

[54] RISING BRACKET PROSTHESIS FOR IMPLANTATION IN MIDDLE EAR

[75] Inventor: Daniel F. á Wengen, Basel, Switzerland

[73] Assignee: Heinz Kurz GmbH Medizintechnik, Dusslingen, Germany

[21] Appl. No.: 08/866,905

[22] Filed: May 30, 1997

[30] Foreign Application Priority Data

May 31, 1996 [DE] Germany ................ 296 09 687 U

[51] Int. Cl.⁶ ........................................ A61F 2/18
[52] U.S. Cl. ............................................. 623/10
[58] Field of Search ................... 623/10, 11, 12

[56] References Cited

U.S. PATENT DOCUMENTS

| | | | |
|---|---|---|---|
| 3,711,869 | 1/1973 | Shea, Jr. ......................... | 623/10 |
| 3,722,003 | 3/1973 | Walchle . | |
| 3,823,423 | 7/1974 | Mercandino ..................... | 623/10 |
| 3,838,468 | 10/1974 | Armstrong ..................... | 623/10 |
| 4,130,905 | 12/1978 | Mercandino ..................... | 623/10 |
| 5,104,401 | 4/1992 | Kurz ............................... | 623/10 |
| 5,306,299 | 4/1994 | Applebaum ..................... | 623/10 |
| 5,370,689 | 12/1994 | Causse ........................... | 623/10 |
| 5,514,177 | 5/1996 | Kurz et al. ...................... | 623/10 |

FOREIGN PATENT DOCUMENTS

| | | | |
|---|---|---|---|
| 0 563 767 A1 | 10/1993 | European Pat. Off. . | |
| 1.583.971 | 12/1969 | France . | |
| 3 901 796 | 7/1990 | Germany ........................ | 623/10 |
| 1 75 178 | 12/1965 | Russian Federation . | |

Primary Examiner—David J. Isabella
Attorney, Agent, or Firm—Michael J. Striker

[57] ABSTRACT

A rising bracket prosthesis for implantation in a middle ear has a body part mountable on a long anvil projection, and a clip connected with the body part and fittable on the long anvil projection so as to hold the body part on the long anvil projection.

7 Claims, 1 Drawing Sheet

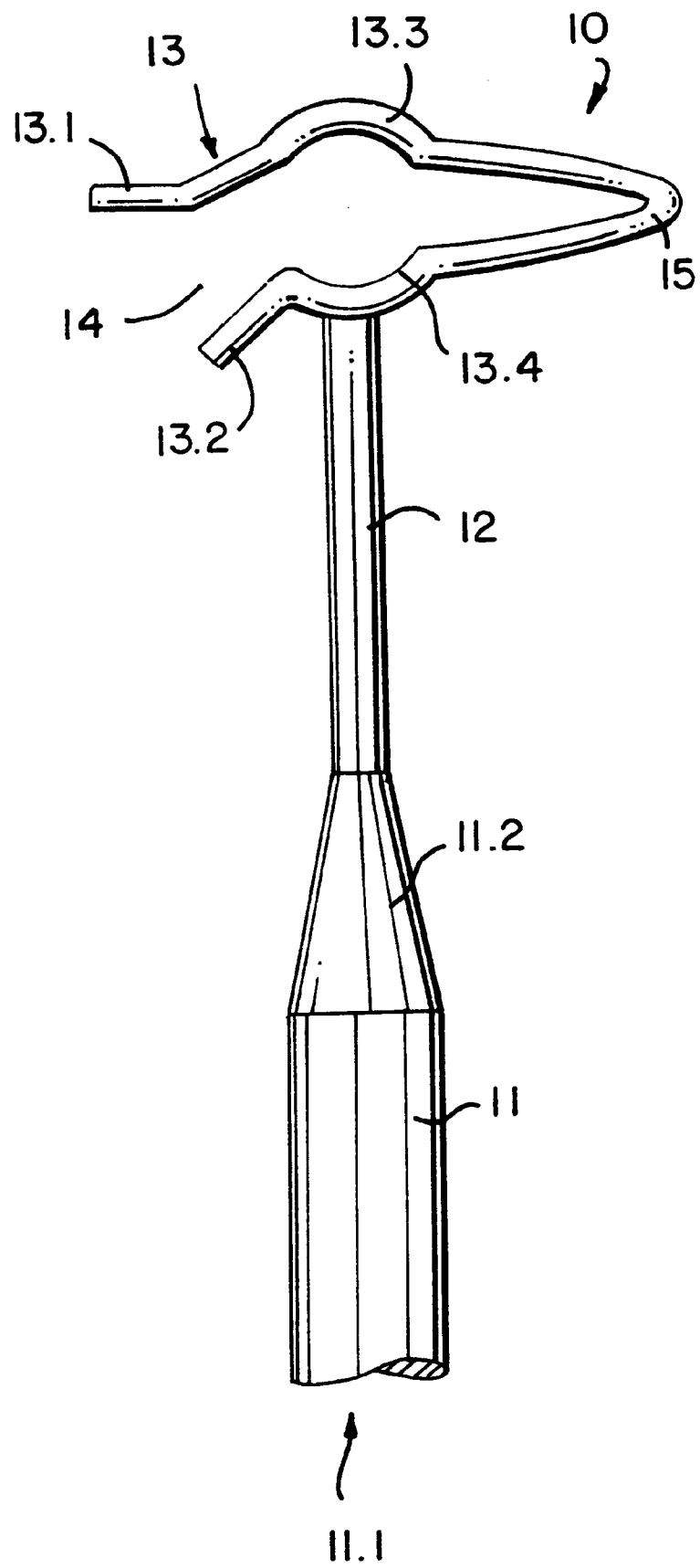

RISING BRACKET PROSTHESIS FOR IMPLANTATION IN MIDDLE EAR

BACKGROUND OF THE INVENTION

The present invention relates to a rising bracket prosthesis for implantation in a middle ear, wherein the prosthesis is mountable on a longer anvil projection.

For sound transmission in a middle ear with defective hearing small bones, several types of prostheses are known. As a replacement for the rising bracket as a rule a prosthesis is utilized, which is composed of a thick piston-shaped part with a slimmer shaft part connected to it. The shaft end is mounted on a long anvil projection. For this purpose, on the shaft end rigid coupling bodies have been used for mounting on the longer anvil projection. The known prostheses, however, frequently lead to narrowing on the long anvil projection, whereby necroses can occur. Also, due to narrowing of a supply vessel an undernourishment of the processus lentcularis can occur. An erosion of the processus lentcularis as a result can lead to the situation that the holding of the prosthesis is no longer guaranteed. Further disadvantages of the known prostheses reside in that the fixation on the long anvil projection in the stapedectomi produces high reaction of the operator.

SUMMARY OF THE INVENTION

Accordingly, it is an object of the present invention to provide a rising bracket prosthesis for implantation in a middle ear, which avoids the disadvantages of the prior art.

More particularly, it is an object of the present invention to provide a prosthesis of the above mentioned type which is simpler to implant.

In keeping with these objects and with others which will become apparent hereinafter one feature of the present invention resides, briefly stated, in a rising bracket prosthesis for implantation in a middle ear, wherein it is provided with an elastic clip which is displaceable on a long anvil projection.

As a result, the rising bracket prosthesis is extremely simple to handle by an operator. The clip is simply fitted on the desired point of the anvil projection. Further mounting means are no longer necessary. The prosthesis is held in its position exclusively by the clamping force of the elastic clip.

In accordance with a further advantages feature of the present invention, the clip can be formed as a one-side open clamp which engages over the long anvil projection after the implantation, locally and in a form-locking manner, so that reliable holding of the prosthesis is guaranteed.

It is advantageous when the clip does not completely surround the long anvil projection. As a result, in contrast to the known prostheses, there is no narrowing of the vessel for the nourishment of the prosthessus lentcularis. By the design of the prosthesis also the danger of the necrose formation is reduced to a minimum.

With the prosthesis designed in accordance with the present invention, after the implantation the clip is arranged on the long anvil projection so that the clip does not abut against the long anvil projection in two regions of the periphery.

In accordance with still a further feature of the present invention, at least the clip can be composed of titanium. The remaining prosthesis can be composed for example of gold. The use of the titanium as a material for the clip has the advantage that it can grow with the anvil projection and therefore the prosthesis obtains an exceptionally reliable holding force.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

The single figure of the drawings is a view showing a prosthesis for implantation in a middle ear in accordance with the present invention.

DESCRIPTION OF PREFERRED EMBODIMENTS

A rising bracket prosthesis in accordance with the present invention is shown in a side view in the drawing and identified with reference numeral 10. The prosthesis 10 has a piston-shaped part 11 which abuts with its lower end side 11.1 on a window and therefore transmits the sound to an inner ear. The piston-shaped part 11 has a narrowing zone 11.2 extending upwardly from the end side 11.1. A prosthesis shaft 12 is connected with the narrowing zone 11.2.

A clip 13 composed of an elastic material is arranged on the upper end of the shaft 12. The clip 13 is formed as a one-side open clamp. It has an opening 14 with which it can be fitted on the long anvil projection. The fitting is further facilitated by the outwardly bent end portions 13.1 and 13.2 of the clip 13.

After the implantation the clip 13 surrounds with its two opposite regions 13.3 and 13.4 the long anvil projection in a form-locking manner. Thereby the supply vessel for the long anvil projection is contacted only in these both opposite regions. The remaining vessel extends in the region of the opening 14 of the clip 13, and also in the region of an arcuate portion 15. The arcuate portion 15 connects the both regions 13.3 and 13.4 at a side 15 which is opposite to the opening 14 and extends at a small distance from an outer surface of the long anvil projection.

Also, in the region of the arcuate portion 15, the supply vessel has a sufficient space.

The above described prosthesis is very easy to handle, and also it prevents a simultaneous narrowing on the long anvil projection. The nourishment on the anvil projection is thereby not interrupted so that it remains healthy.

The clip 13 can be composed preferably from titanium. Thereby an intergrowth of the clip 13 with the material of the bone of the long anvil projection is possible. The remaining portion of the prosthesis can be composed of gold.

It will be understood that each of the elements described above, or two or more together, may also find a useful application in other types of constructions differing from the types described above.

While the invention has been illustrated and described as embodied in rising bracket prosthesis for implantation in middle ear, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A rising bracket prosthesis for implantation in a middle ear, comprising a body part mountable on a long anvil projection; and an elastic clip connected with said body part and fittable on the long anvil projection so as to hold said body part on the long anvil projection, said clip being formed as a one-side open clamp which is adapted to incompletely surround the long anvil projection after the implantation locally in a form-locking manner, said clip being formed so that when after the implantation it is arranged on the long anvil projection, it does not abut against the long anvil projection in two regions of a periphery of the long anvil projection, said clip having an opening and two end portions arranged around said opening and bent outward from said opening.

2. A rising bracket as defined in claim 1, wherein said clip is composed of an elastic material.

3. A rising bracket as defined in claim 1, wherein said clip has two central portions extending from said end portions, and an opposite end portion which is located opposite to said opening and connects said portions with one another.

4. A rising bracket as defined in claim 3, wherein said opposite end portion is arcuate.

5. A rising bracket as defined in claim 1, wherein said clip is composed of titanium.

6. A rising bracket as defined in claim 1, wherein said body is composed of gold.

7. A rising bracket as defined in claim 1, wherein said clip extends transversely to said body.

* * * * *